(12) United States Patent
Russo et al.

(10) Patent No.: US 12,190,748 B2
(45) Date of Patent: Jan. 7, 2025

(54) DEVICE FOR ASSISTING THE AMBULATION WITH MEASURING OF THE POSITION AND REMOTE ASSISTANCE

(71) Applicants: QuicklyPRO Srl, Bergamo (IT); Università degli Studi di Bergamo, Bergamo (IT)

(72) Inventors: Davide Russo, Florence (IT); Alessio Valgimigli, Florence (IT); Niccolò Sala, Gazzaniga (IT)

( * ) Notice: Subject to any disclaimer, the term of this patent is extended or adjusted under 35 U.S.C. 154(b) by 426 days.

(21) Appl. No.: 17/627,668

(22) PCT Filed: Aug. 11, 2020

(86) PCT No.: PCT/IB2020/057541
§ 371 (c)(1),
(2) Date: Jan. 15, 2022

(87) PCT Pub. No.: WO2021/028829
PCT Pub. Date: Feb. 18, 2021

(65) Prior Publication Data
US 2022/0246059 A1    Aug. 4, 2022

(30) Foreign Application Priority Data

Aug. 12, 2019  (IT) .................... 102019000014640

(51) Int. Cl.
| | |
|---|---|
| G09B 19/00 | (2006.01) |
| A61B 5/00 | (2006.01) |
| A61B 5/11 | (2006.01) |
| G08B 5/36 | (2006.01) |

(Continued)

(52) U.S. Cl.
CPC .......... G09B 19/003 (2013.01); A61B 5/0022 (2013.01); A61B 5/11 (2013.01); G08B 5/36 (2013.01); G08B 7/066 (2013.01); H05B 47/115 (2020.01); *A61B 2562/0219* (2013.01)

(58) Field of Classification Search
CPC .... G09B 19/00; G09B 19/003; H05B 47/115; A61B 5/0022; A61B 5/11; A61B 5/36; A61B 2562/0219; G08B 7/066
See application file for complete search history.

(56) References Cited

U.S. PATENT DOCUMENTS

| | | | |
|---|---|---|---|
| 2016/0045386 A1* | 2/2016 | Sandler | A61B 5/7455 623/24 |
| 2019/0053713 A1* | 2/2019 | DeBates | F24F 13/30 |
| 2019/0298998 A1* | 10/2019 | Coleman | A61B 5/389 |

FOREIGN PATENT DOCUMENTS

| | | |
|---|---|---|
| CN | 106063987 | 11/2016 |
| KR | 101647629 | 8/2016 |
| WO | 2019069217 | 4/2019 |

* cited by examiner

*Primary Examiner* — Timothy A Musselman
(74) *Attorney, Agent, or Firm* — Themis Law (57) ABSTRACT

A wearable device for assistance to ambulation includes a support, a power supply, a light source, sensors, a processing unit configured to control the activation and deactivation of the light source during ambulation, a measuring member, detecting and/or transmitting the linear and/or angular variation of the position of at least part of the body of a person to whom the wearable device is coupled, and a local station and/or a station connected remotely through a telecommunication network for processing data coming from the measuring member. A method for assisting the ambulation of a person with such wearable device is also disclosed.

20 Claims, 9 Drawing Sheets

(51) Int. Cl.
*G08B 7/06* (2006.01)
*H05B 47/115* (2020.01)

DEVICE FOR ASSISTING THE AMBULATION WITH MEASURING OF THE POSITION AND REMOTE ASSISTANCE

Object of the present invention is an ambulation assistance wearable device and a corresponding method according to the preambles of the corresponding independent claims.

The present invention is specifically applicable to the field of the rehabilitation of people with mobility problems, for example, during the recovering step after a surgery or an accident or suffering from medical conditions such as Parkinson's disease or other diseases causing, indeed, mobility problems.

Referring in particular to Parkinson's disease, a common problem affecting people suffering from such a disease is the "freezing", i.e. a disorder whereby a person feels the urge to walk, but cannot lift the feet from the ground in order to make steps.

Different devices attempting to solve the "freezing" problem and, more generally the ambulation assistance issue, have been developed over years. Such devices provide for projecting a visible light, also called marker in jargon, to the ground, in front and at some distance from a person. The marker, which a person is asked to pass with a step, has for example the shape of a line perpendicular to the forward direction or any desired additional shape like a bright spot or brighter than the ambulation ground.

Devices of this kind are known since long time, as for example it is described in document WO2019069217 (A1) owned by the same applicant. In this document a system and a corresponding method are disclosed for controlling the ambulation, which are able to help the rehabilitation of the person afflicted by a pathology thanks to markers which are projected against the sole, the said marker being made stable during the alternate displacement of the lower limbs, this means by acting against the displacements and the rotations of the light sources and/or of the reflection mechanisms which are involved in controlling said markers. Same document WO2019069217 discloses furthermore at least one control parameter (Pc) associated to one or more control signals (Sc), wherein the said at least one control parameter (Pc) corresponds to an angle or to a displacement measure correlated to the instant position of at least one part of the body of the person wearing the device during the ambulation. In the above mentioned patent, applying the said control parameter with the said relating control signals helps surely in stabilizing the marker as the indicated aim, but the measure of the displacements and/or of the torsions is limited to the control signals involved within the body of the person wearing the device and thus affected by imprecision of the measures and particularly in a context as the one of the motion difficulties which implicitly define irregular conditions of movements and/or movements which are not easily predictable on the base of common anatomical dynamics of persons not affected by pathologies relating to the autonomous movements of a person.

Furthermore, the known art of the state of the art limits the actions based on the said control parameter to actions of corrections of the positioning of the marker at the soil, based on the punctual state of ambulation but does not allow the interaction with external apparatuses for analyzing in real time or in a differed time and/or in the space by means of specialized personnel, the said specialized personnel being able to act aiming the improvement if the therapy involving the person wearing the present device.

Therefore, there is the need for improving the state of the art involved in the ambulation assistance, as disclosed in WO2019069217 in order to overcome the afore mentioned limits.

The main object of the present invention is therefore to provide an ambulation assistance wearable device and a corresponding method, which allow project a luminous footprint on the ground, the said footprint being stabilized also as a function of the instant and/or following status of the ambulation improving the phases of acquiring the parameters which describes the motion of the said ambulation.

Another object of the present invention is to provide a wearable device and the corresponding method for assisting ambulation, the said deice and the said method being able to measure the effective motion of ambulation of the person wearing the device with a precision of measuring which is suited to the aims of correct positioning of the marker at the ground, the said precision of measure the difference between the effective value of the motion parameters and what has been measured by special devices apt to the reach the aim and being intended as adequate a precision of the measure in the range between 1 millimeter and 50 centimeters, preferably in the vicinity of 5 centimeters.

Still another object of the invention is to provide an ambulation assistance wearable device and a corresponding method, which measures the effective ambulation motion of a person wearing the device and which device processes the parameters describing of the ambulation motion in an electronic form such that these parameters can be made available to specialized operators and/or to medical devices being involved in the treatment of the pathology, the said specialized operators and/or the said medical devices being able to operate locally and/or remotely by means of telecommunication technologies which are known at the state of the art and/or which will be implemented in future.

These and still other objects of the present invention will be more evident from the following description of some exemplary embodiments illustrated in the accompanying drawings wherein.

Current state of the art comprises a plurality of devices for assisting ambulation which has been developed in the course of years and many of which employs visual techniques comprising the projection of luminous footprints at the ground having different shapes and/or intensities and/or colors in order to be suited to the patient suffering a pathology such as Parkinson syndrome or in general pathologies implying motion difficulties and/or of coordination between the lower limbs and the signals for stimulating the execution of one or more steps in a desired direction. The medical concept of rehabilitation is clearly not part of the present invention as well as the involved pathologies but it is worth noticing that in some neurophysiological conditions a rehabilitation path can be considered satisfactory also if it is able to slow down the degenerative processes of the condition of the patient, particularly when such patient has a high age and is thus potentially limited in relation to the capacity of recover.

Therefore it is important that the tool to be used for the ambulation offers the maximum of effectiveness in the assistance action to said ambulation and also it is important to be able to monitoring the behavior of the person during motion in such a way to be able to describe the punctual behavior and/or the behavior during different sessions of the rehabilitation treatment in order to be able to define the parametrization of the devices which better suites the medical treatment or the specific patient.

Document WO2019069217 of the same applicant and which description is used as a reference ed is incorporated as a part of this invention, provides for a system and a corresponding method for controlling of the ambulation which is able to help the rehabilitation of the person suffering of a pathology by means of markers projected to the ground, the said markers being made stable during the alternate movement of the lower limbs for example by opposing to the displacements and/or rotations of the light sources and/or of the reflection arrangements involved in the control of the said markers. Same document WO2019069217 indicates at least one control parameter (Pc) associated to one or more control signals (Sc), where the said at least one control parameter (Pc) corresponds to an angle or to a displacement measure correlated to the instant position of at least one part of the body of the person wearing the device during the ambulation.

Basing on document WO2019069217, the applicant has found the need of improving the operative capacities and the present invention refers to a wearable device for assisting the ambulation comprising:

at least one support intended to be removably attached to the body of a person, in a respective attachment position;

at least power supply unit attached to the said at least one support;

at least a light source mounted on the said at least one support and electrically connected to the said at least one power supply unit, the said at least one light source being intended, in use, to emit at least one beam of visible light towards the ground, at least at one front stepping point to which the person has to move the foot to move forward along a direction of ambulation;

at least sensors intended to detect at least one control parameter ($p_c$) identifying the ambulation condition;

at least one processing unit which is operatively connected, to the said at least one power supply unit, said at least one light source and said at least one sensor units, being intended to control the activation-deactivation of said at least one light source as a function of said at least one control parameter corresponding to an angle or a displacement measurement related to the instant position of at least one part of the body of the person which, during ambulation, wears the device;

at least a unit provided for measuring, saving and/or transmitting a linear and/or angular variation of the position of a part of the body of the person to which the said ambulation assistance device refers and being the said at least one control parameter determined at least one time instant and at least as a function of the said at least one unit measuring the linear and/or angular variation of the position of at least one part of the body of the person to which the said ambulation assistance device refers.

Figure 1:
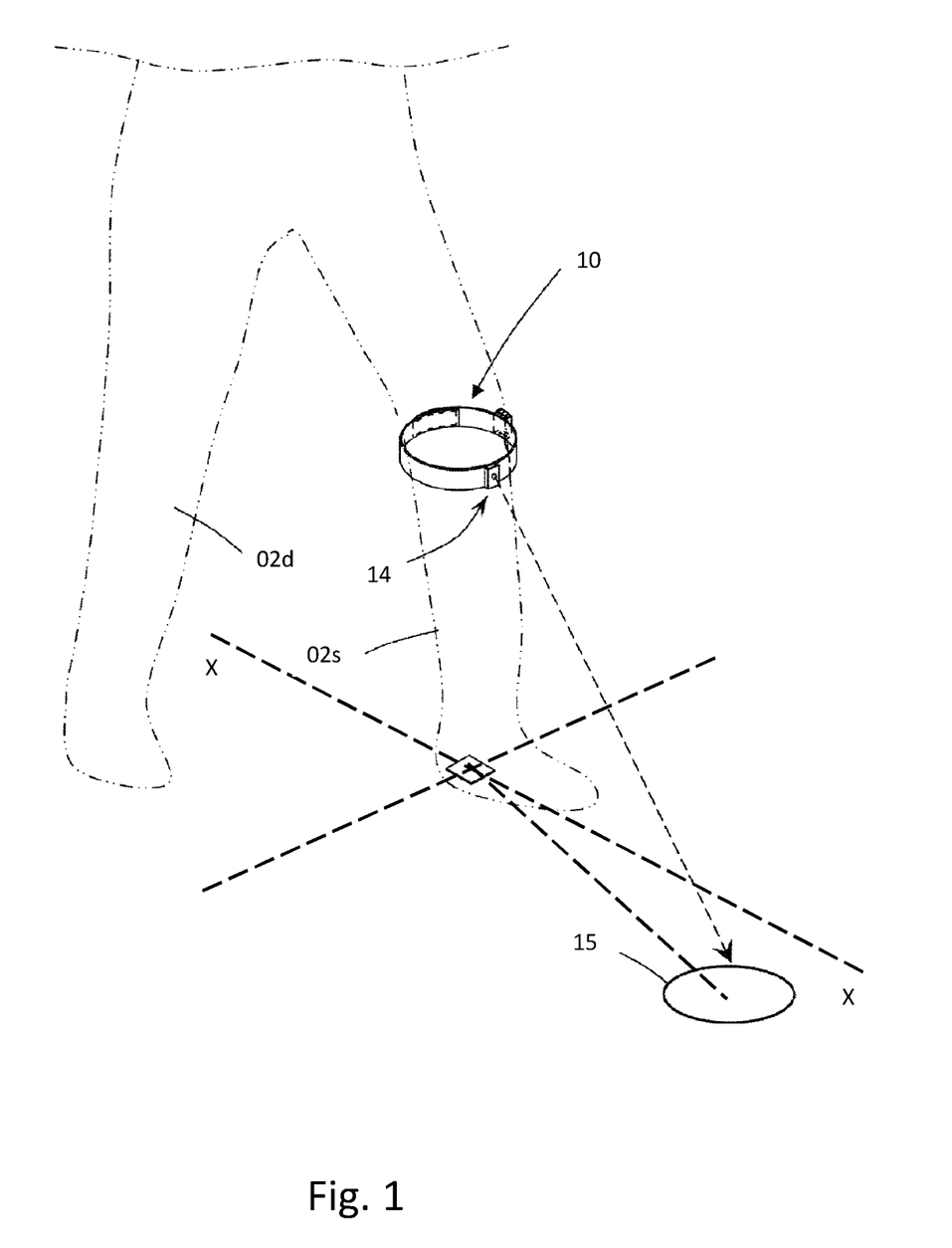
FIG. 1 shows an embodiment of an ambulation assistance device according to the known art, which embodiment is placed at the knee and providing as footprint at the ground having elliptic shape which footprint is directly irradiated by a light source.

According to the present invention, one or more organs are involved for determining the position and thus the variation of the said position in the space for describing the ambulation of the patient approximately along a direction of moving forward x-x as in FIG. 1. The said organs can be positioned or cam be worn at different parts of the body which are in motion during the act of ambulation; although it is more frequent the positioning at the lower limbs, this is not strictly needed and the use at other parts of the body such as for example the thorax and/or the abdomen falls within the scope of the invention which operating criterion disregards the said specific aspects.

The specific embodiment is also in relation to the used technology which adoption must consider the quality of the achievable results but also other aspects such as for example the simplicity of construction and the practicality of use, the choice of the signals involved in the measuring of the motion: the current measuring technologies provides for a large range of methods for measuring a distance and a good number of these rely on physical criterion according to which a waveform propagating in space, optionally supported by a transmissive medium, needs a certain time to run across a certain distance; frequently used technologies which are known since long time to the experts in the art comprise, for example, ultrasound signals, electromagnetic radiation owing to the spectral range of the radio waves or of the microwaves (also known with the acronyms of anglophone origin RADAR), the light beams suitably amplified (known under the acronyms of anglophone origin LASER).

Figure 2A:
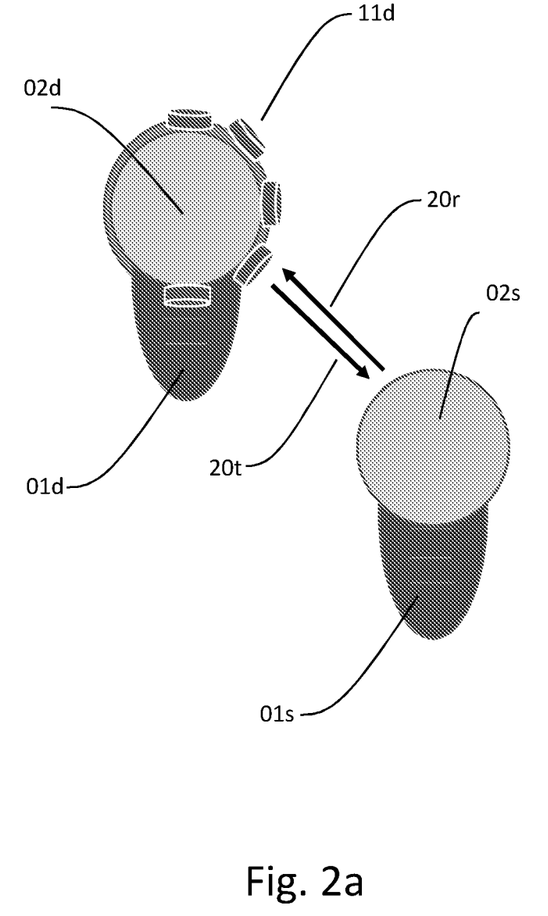
FIGS. 2a and 2b show an upper view of two independent embodiments in which the device is provided of multiple sensors and is worn in whichever point of the thigh, of the knee or of the leg (FIG. 2a) or at the feet (FIG. 2b) of the person intended to be helped by the device.

In an embodiment describe in FIG. 2a, the device is worn only on the left limb 02d and there are provided receiving/transmitting devices 11d which are placed in a plane substantially parallel relatively to the transversal plane of the body of the person in order to cover within said plane an angle of 180° the corresponding arch being centered on the lateral-lateral axis of the person and being oriented in the direction of the opposed knee; in this embodiment, 5 equally distanced devices are used for measuring the distance relatively to objects in front of or behind of the person and also in relation of the left limb $02s$. The measure is carried out by means of a transmitted signal $20t$ which is reflected in form of a signal $20r$ a wearable equipment being possibly provided in the vicinity of the alleged reflection zone and being advantageously adaptable to the shape of the body of the person, said equipment being characterized by reflection properties related to the technology of receiving/transmitting used and the said equipment being able to contribute to the reflection of the signals used by the device within the scope of the invention.

Figure 2B:
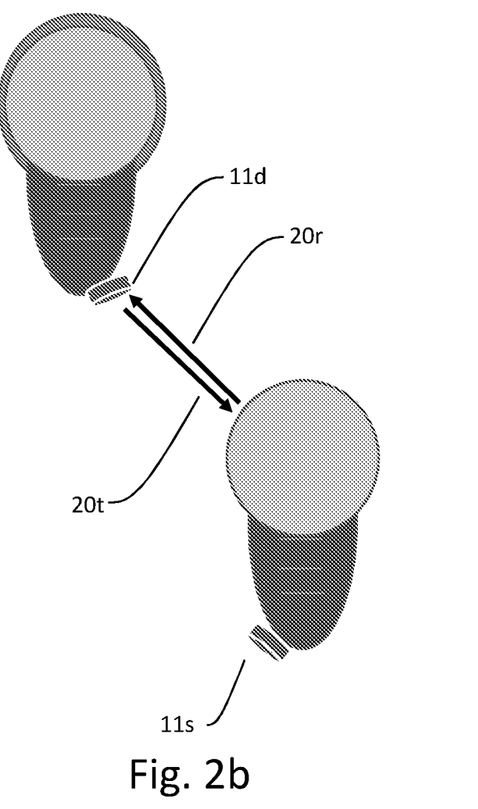

An alternative embodiment of the one just described, provides receiving/transmitting devices which are positioned at the tip of the foot, as shown in FIG. $2b$. form the comparison with the preceding figure, it appears that that the number of devices is reduced and this is justified by the intention of limiting the measure only to the distance between the extremities of the person and in particular between the right foot $01d$ and the left foot $01s$ when the said left foot $01s$ is positioned before the said right foot; an analogous measure is then carried out with inverted feet and is alternated in the course of the ambulation.

Figure 3A:
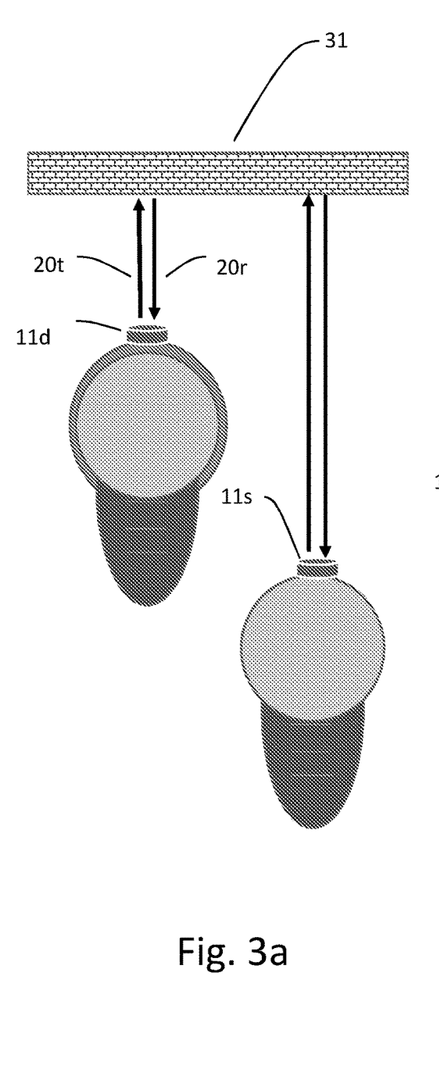
FIGS. 3a and 3b illustrate an upper view two further independent embodiments in which the device is used for measuring the parameters of displacement relatively to an external surface such as for example a wall.
Figure 3B:
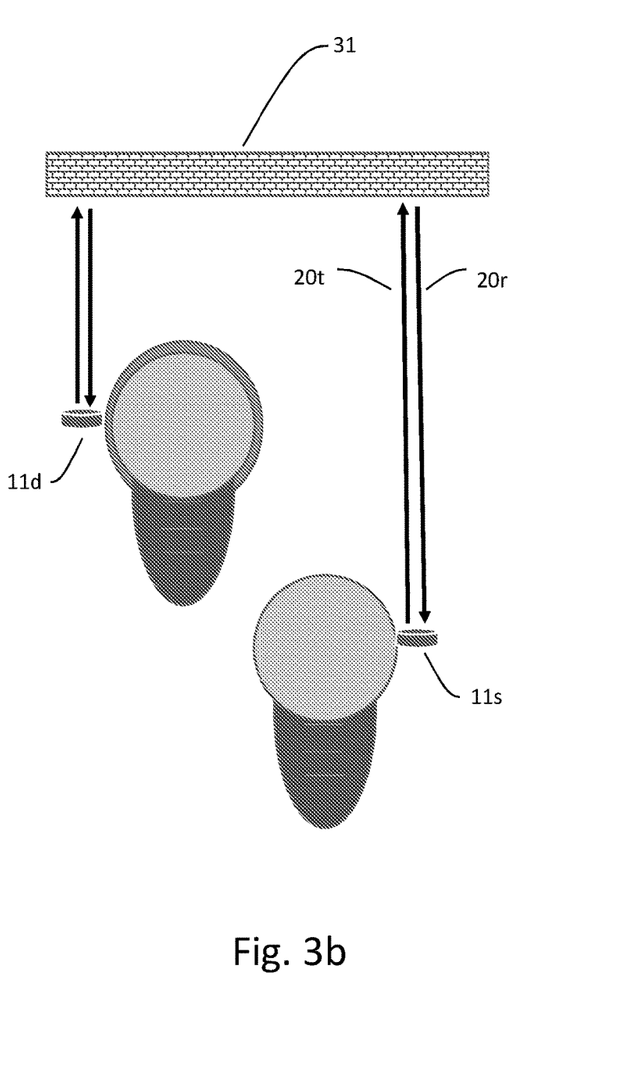

FIGS. $3a$ and $3b$ show a particular embodiment which presupposes the existence of a stable plane surface, as for example the wall of a room 31, which wall is placed parallel to the frontal plane of the person and precisely to the shoulders. Also in this embodiment, the invention uses the reflection of known signals, with a signal $20t$ emitted along the sagittal axis and a received signal $20r$ after the interaction with the said wall of a room 31. In the representation only one unit $11d$ is responsible of the processing of both known signals $20t$ and $20r$; a correspondent unit $11s$ is provided which can be worn on the other limb and having identical functions and said units $11d$ and $11s$ can be positioned at the center or in an external lateral position as respectively according to FIG. $3a$ or $3b$. One can notice the reference to a transmitted signal $20t$ and to a reflected signal $20r$ which are referred to a device $11d$ on the right limb and to an analogous configuration of a second device $11s$ on the left limb: the said devices $11d$ and $11s$ are activated alternatively as a function of the motion of the limb to which they refer, for example basing on where the weight of the body is positioned during the ambulation disactivating the device where the pressure is higher, this means for the limb which remains at rest relatively to the ground during the step.

Figure 4:
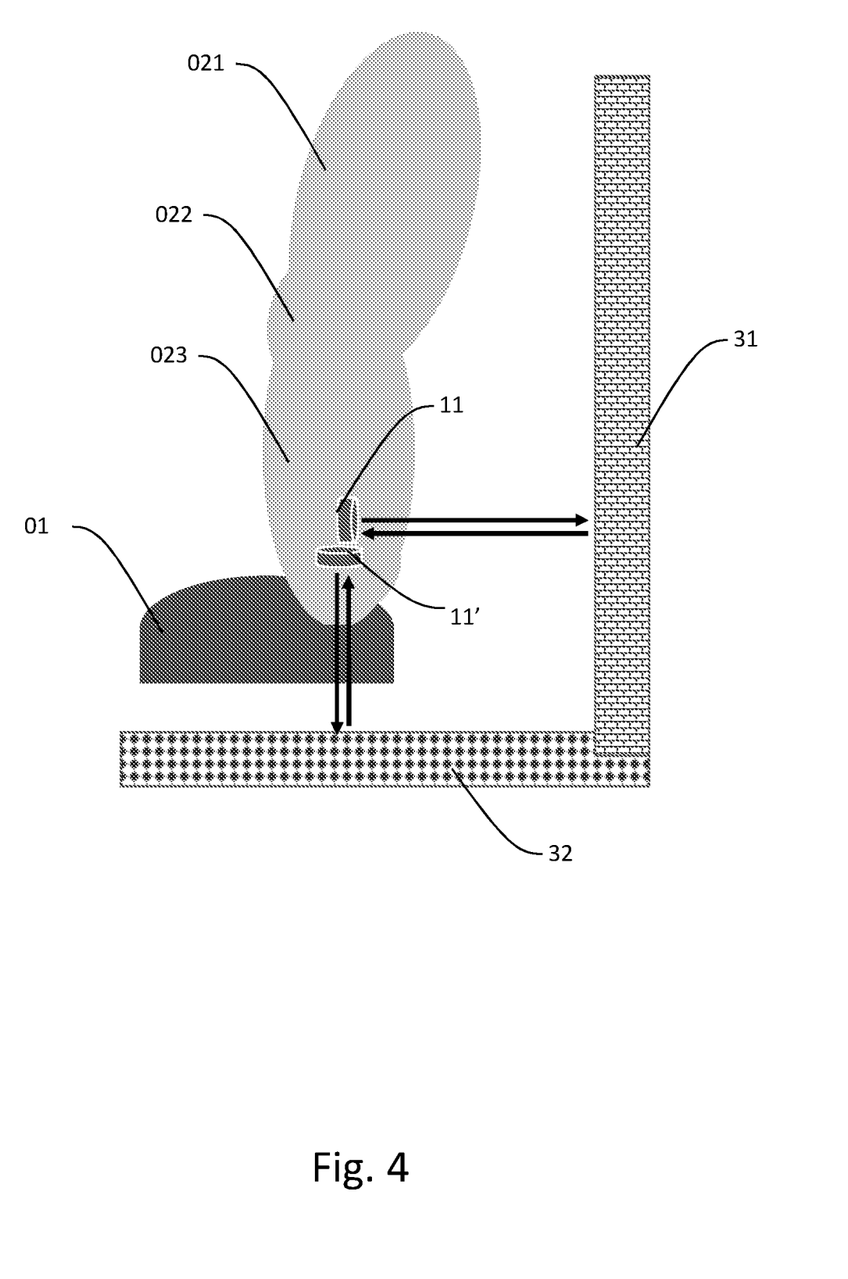
FIG. 4 shows a further embodiment according to a side view of the lower limbs where the device is used for determining the parameters of displacement relatively to two external surfaces and particularly a wall and the ground.

As then shown in FIG. 4, another embodiment provides for an additional device for determining the displacement of the foot 01 relatively to the ground 32; it is worth observing that in this implementation there are present for constructive simplicity, two sensors 11, 11' which are oriented at 90° and that for sake of the implementation choice said sensors are positioned at the lower part of the leg 023, which position can be modified without affecting the functionality of the invention once there is a correct parametrization.

Figures 5A, 5B:
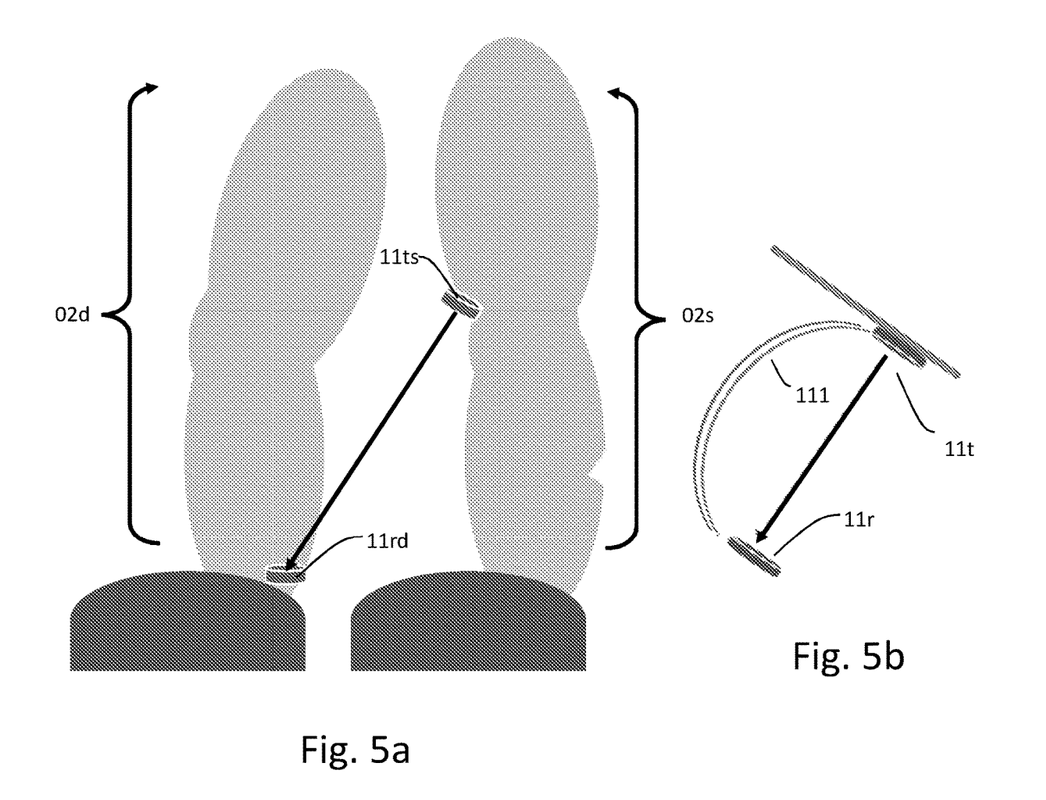
FIG. 5a shows an embodiment in which the device achieves the aims thanks to a source and a receiver which are separated and placed respectively at the knee of a lower limb and at the feet of the other lower limb of the walking person.
FIG. 5b show a two wire connection between the said source and the said receiver as a return mean of the transmitted signal.

The further embodiment of FIG. $5a$ implements in a different way the teaching of reflection by means of the separation of the functions of transmitting and receiving which are carried out by different physical devices and which re differently positioned on the body of the patient. In this implementation, which makes use of two different kinds of signals and preferably of electromagnetic and ultrasound, the waveform generated by a transmitting unit $11ts$ is propagated by means of acoustic waveforms at a non audible frequency towards a receiving unit $11rd$, which receiving unit is connected by means of one or more conductors 111 to the said transmitting unit $11ts$ (FIG. $5b$). Thus two different transmitting means are present which features are a priori known and particularly the propagation speed can be used for defining at each time instant the reciprocal displacement between transmitting unit $11s$ and receiving unit $11rd$ and as an immediate consequence for defining the ambulation motion of the patient. The embodiment shown in FIG. $5a$ provides the positioning of a transmitting unit $11ts$ approximately at the knee of the left leg $02s$ and the positioning of the receiving unit about the heel of the right leg $02d$, however the invention can achieve the prefixed aims also involving different parts of the body of the person having ambulation difficulties.

A further preferred embodiment is described with the help of the figures from 6 to 9. A wearable device according to the disclosure of document WO2019069217 comprises at least one support 10 destined to be secured to the body of a person in a removable way, in a position of securing in the proximity of the knee $022s$ of the person. Said support 10 has the function of containing various organs of the system for assisting the ambulation among which the optical source $14s$ which in figure is represented during one of the possible projection phases of a luminous marked 11 on the ground approximately along a direction of moving forward x-x as described in FIG. 1 and the said optical source comprises actuation means destined according to what has been already disclosed in document WO2019069217 to allow the displacement in a plane substantially perpendicular to the ground and parallel to the direction of moving forward x-x in proximity of the opposed leg $02d$.

Figure 6:
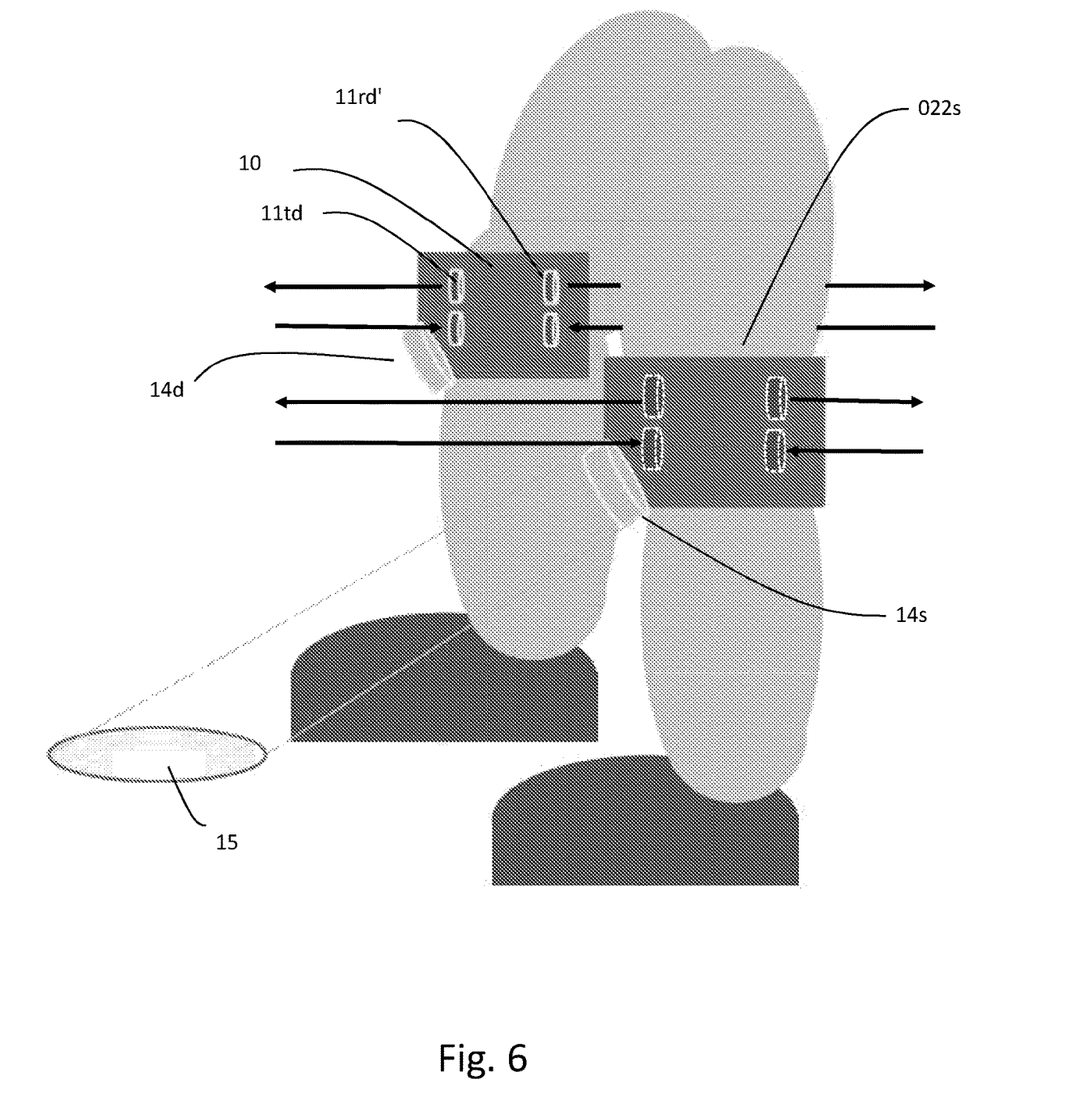
FIG. 6 shows an external side view parallel to the sagittal plane of a preferred embodiment in which the device is worn by both lower limbs at the level of the knee and in which the device operates by means of the reflection in a plurality of directions.
Figure 7:
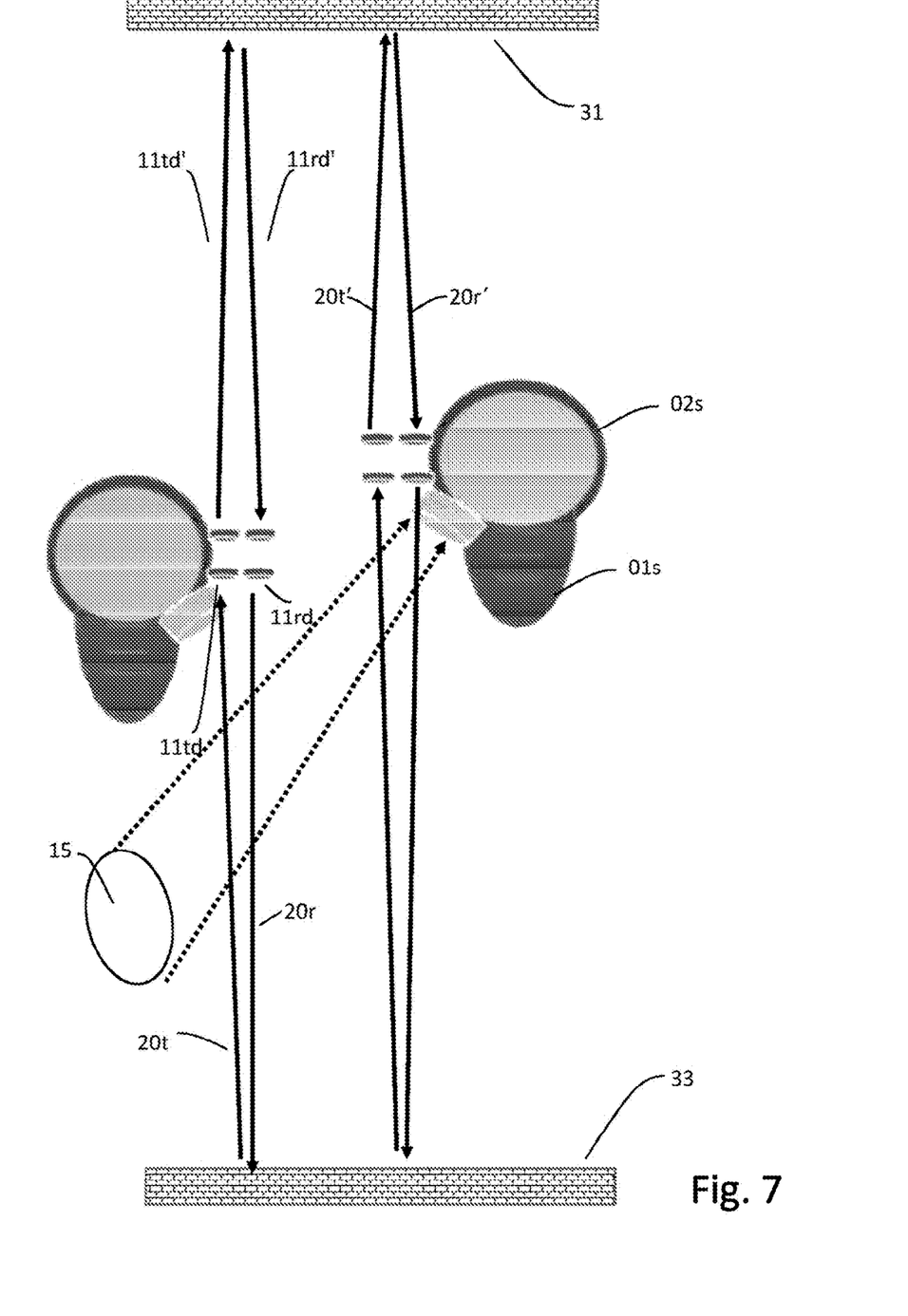
FIG. 7 shows an upper view of the device according to FIG. 6 and with a reception/transmission towards two surface which are parallel to the frontal plane of the person wearing the device.

On the said support 10 there are secured also two couples of devices ($11td$, $11rd$), ($11td'$, $11rd'$) which are used respectively for measuring the distance towards the posterior wall 31 and for measuring the distance towards the anterior wall 33 where it is intended that the distance is measured in relation to the time that the electromagnetic signal and/or the acoustic vibrations need to run across the said distance and considering the field of use of the present invention the hypothesis is made that the propagation speed of the transmitted signals $11td$, $11td'$ and of the reflected signals $11rd$, $11rd'$ is at least two orders of magnitude higher than the speed associated to the motion of ambulation also in the case of signals propagating with a low speeds such as for example acoustic waves.

Possible environmental interferences due to external sources of signals such as for example electromagnetic noise or acoustic noise can be limited by transmitting signals characterized by predetermined wave forms such as for example pulse sequences having variable frequency and/or temporal length and/or sinusoidal waves of known frequency such as to be recognized in an univocal way in the receiving phase. Advantageously, said transmitter can be activated in a predetermined sequence in order to identify in an univocal way the origin of the signal at a precise time instant and thus in limit the non-desired interference effects with the sources internal to the device.

In this embodiment a second wearable device is further provided which operates in an analogous manner as above described but in a symmetric configuration relatively to the sagittal plane of the person, which in fact projects the marker for helping the movements of the corresponding leg by measuring the displacement of the leg to which the said device is secured.

This embodiment shows therefore a possible configuration of a device which is able to measure, as widely disclosed before, the parameters of distance from a reference which in the present form consists in one or more external walls forming a reference being external to the person wearing the device.

Figure 8:
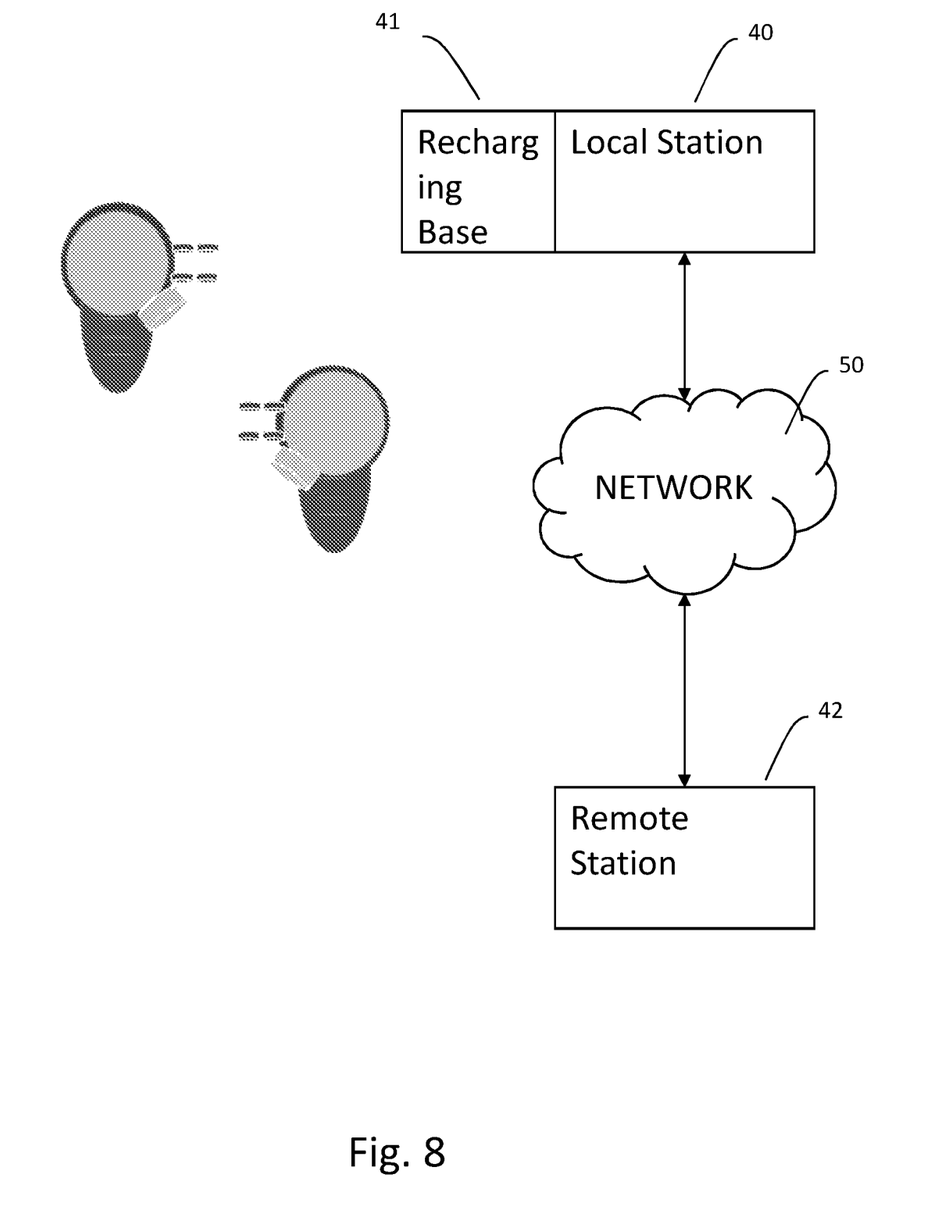
FIG. 8 shows the device according to FIG. 6 further comprising a local station for assisting operations such as reception and transmission and/or processing and or displaying the motion parameters and for assisting to the charging of the wearable device in an embodiment comprising such functions.

From the description of the embodiments shown herein, it can be deduced the presence of a method and of a device able to determine with an adequate precision the temporal position at a certain instant and consequently the availability of a set of information which suitably processed can define the motion of the patient as a function of the linear velocity and/or of the angular velocity intended as a variation of the space in the time unit, a feature which can advantageously help the analysis of the locomotory behavior of the person and thus validate the effectiveness of the assistance also in order to ameliorate the parameters which regulates the behavior of the device as disclosed in the reference document WO2019069217. In order to enhance the possibility of analyzing and using the harvested information during the operative phases, the present invention comprises a local processing station 40, optionally integrated with a module for energy recharging of the wearable device which can be provided as a base for the restoration of possible rechargeable energy sources provided by the wearable device.

Figure 9:
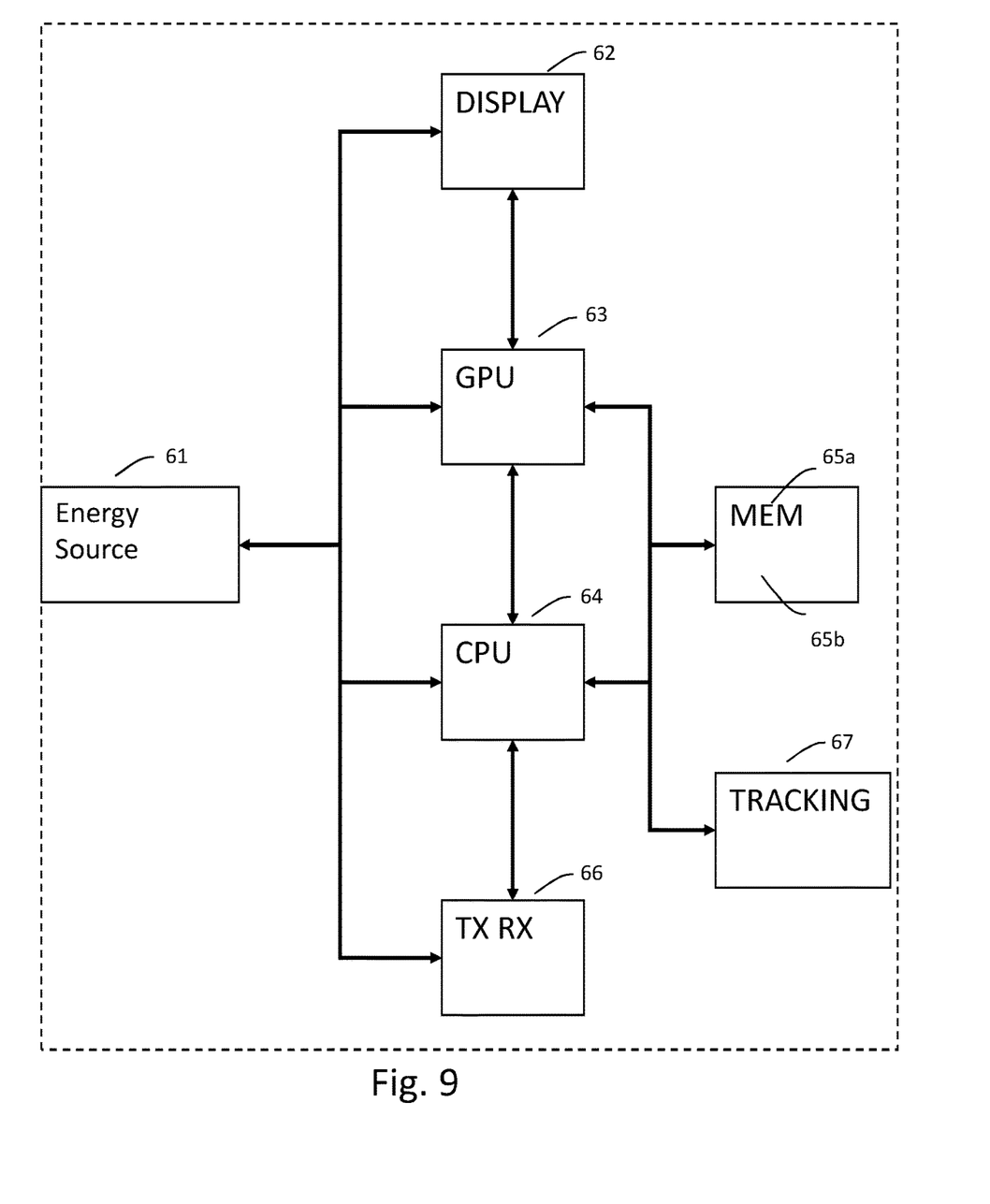
FIG. 9 shows a possible embodiment of a local or remote support station according to FIG. 8.

This local processing station, of which a possible block diagram is represented in FIG. 9, comprises at least one power supply unit 61, at least one processing unit comprising at least an electronic processor 64, at least a nonvolatile memory unit 65a, at least one volatile memory unit 65b, at least a module for receiving information coming from the device 66, at least a graphic processing unit 63 and at least a display unit 62 and the said organs are defined with the aim of supporting one or more processing algorithm of the data coming from the sensors by means of a set of operative instructions coded as part of a processing program.

The invention comprises said unit in order to be able to process and thus render available to the doctor, but also to the patient itself, a set of data generated by the wearable device, harvested by the receiving/transmitting unit 66 and stored in one or more memory units 65a, 65b. depending from the processing algorithm the said data can be presented in the form of a simple time sequence of displacement and which can further be analyzed by the graphic unit 63, generally known with acronym of anglophone origin GPU, in order to present to the doctor or to the patient the said set of data in the graphic form optimally multidimensional or in another form known to the skilled person and aimed to help the reading of the data and the definition of ameliorating actions of the ambulation.

The local station comprises furthermore a tracking module 67 which is provided for managing the control parameters of the device which, as discloses, can be regulated relating to at least one of its control parameter in such a way to maximize the effectiveness of the processing for progressive steps also as a function of the measurements that the wearable device carries out during the application to the patient.

Finally there is provided the at least part of the functions of the said local station can be replicated and or comprised in a remote station 42 connected by means of one or more telecommunication infrastructures 50 in such a way to render available the maximum possible number of functionalities of the said local station also to operators or apparatuses at whatever geographic distance from the site at which the therapy is carried out so to be able to contribute to the said therapy without being physically present following the modern practice of telemedicine.

From the above disclosure it appears evident that the too according to the invention achieves the prefixed aims.

The subject of the invention can undergo many modifications and variations, each falling within the inventive concept which is expressed in the annexed claims. All the particulars may be substituted by other elements being technically equivalent and the materials can be different depending from the needs without abandoning the scope of protection of the present invention.

Although the subject matter has been described with particular reference to the annexed figures, the reference number used in the description and in the claims are used only for ameliorating the understanding of the invention and does not constitute any limitation of the claimed scope of protection.

The invention claimed is:

1. An ambulation assistance wearable device, comprising:
   at least one support, adapted to be removably attached to a body of a person in an attachment position;
   at least one power supply, anchored to said at least one support;
   at least one light source, mounted on said at least one support and electrically connected to said at least one power supply, said at least one light source being configured, in use, to emit at least one beam of visible light towards a ground, at least at one front stepping point to which the person has to move a foot, in order to move forward along an ambulation direction;
   at least one sensor means configured to detect at least one control parameter identifying an ambulation condition;
   at least one processing unit operatively connected to said at least one power supply, said at least one light source and said at least one sensor and configured to control an activation-deactivation of said at least one light source, as a function of said at least one control parameter, corresponding to an angle or to a displacement measurement related to an instant position of at least one part of the body wearing the ambulation assistance wearable device during ambulation;
   at least one measuring member configured to measure, save, and/or transmit a linear or an angular variation of the position of at least one part of the body of the person, to which assistance to ambulation makes is provided,
   wherein said at least one control parameter is determined at least at one time instant and at least as a function of said at least one measuring member of the linear and/or the angular variation of the position of at least one part of the body of the person, to whom the said assistance to the ambulation is provided,
   wherein said at least one measuring member comprises at least one signal source and at least one signal receiver, said at least one measuring member being configured to quantify a reciprocal and/or absolute positioning of said at least one signal source and of said at least one signal receiver, and
   wherein said at least one measuring member comprises at least one accessory adaptable to a body shape of the person to whom said at least one measuring member is applied in an arbitrary position, said at least one accessory having reflecting properties combined with transceiving technologies and said accessory being configured to contribute to a reflection of the signals used by the ambulation assistance wearable device.

2. The ambulation assistance wearable device according to claim 1, wherein said at least one measuring member determines a variation of the position by analyzing a propagation in space of signals having predetermined waveforms.

3. The ambulation assistance wearable device according to claim 2, wherein said signals consist of electromagnetic radiation and/or electro-acoustic oscillation phenomena usable to measure displacement.

4. The ambulation assistance wearable device according to claim 2, wherein said at least one measuring member uses one or a combination of said signals propagating in space.

5. The ambulation assistance wearable device according to claim 1, wherein said at least one signal source and wherein said at least one signal receiver use different concurrent and/or delayed transceiving technologies to manage signals having distinct and distinguishable waveforms, said waveforms being able to be emitted contemporaneously or at different times.

6. The ambulation assistance wearable device according to claim 1, wherein said at least one measuring member comprises at least two or more signal sources and/or at least two or more signal receivers operating contemporaneously.

7. The ambulation assistance wearable device according to claim 1, wherein said at least one measuring member further comprises a system that acquires static and/or dynamic images connected to said processing unit in order to process said images during the ambulation and/or in a following time step.

8. The ambulation assistance wearable device according to claim 1, wherein said at least one measuring member uses autonomous systems to determine linear acceleration and/or angular acceleration and/or polar orientation, said autonomous systems comprising accelerometers, gyroscopes and magnetic detectors as inertial measurement units.

9. The ambulation assistance wearable device according to claim 1, wherein said attachment position is at a lower limb and corresponds to one or more different regions of the lower limb bearing said ambulation assistance wearable device.

10. The ambulation assistance wearable device according to claim 1, further comprising a unit managing remote data, implemented as an algorithm, operative steps and instructions of said algorithm being encoded as part of a processing program that can be called up and executed by generic or specific computer platforms, said unit performing actions targeted to an exploitation of the remote data by an operator.

11. An ambulation assistance wearable device, comprising:
at least one support, adapted to be removably attached to a body of a person in an attachment position;
at least one power supply, anchored to said at least one support;
at least one light source, mounted on said at least one support and electrically connected to said at least one power supply, said at least one light source being configured, in use, to emit at least one beam of visible light towards a ground, at least at one front stepping point to which the person has to move a foot, in order to move forward along an ambulation direction;
at least one sensor means configured to detect at least one control parameter identifying an ambulation condition;
at least one processing unit operatively connected to said at least one power supply, said at least one light source and said at least one sensor and configured to control an activation-deactivation of said at least one light source, as a function of said at least one control parameter, corresponding to an angle or to a displacement measurement related to an instant position of at least one part of the body wearing the ambulation assistance wearable device during ambulation;
at least one measuring member configured to measure, save, and/or transmit a linear or an angular variation of the position of at least one part of the body of the person, to which assistance to ambulation makes is provided,
wherein said at least one control parameter is determined at least at one time instant and at least as a function of said at least one measuring member of the linear and/or the angular variation of the position of at least one part of the body of the person, to whom the said assistance to the ambulation is provided,
wherein said at least one measuring member determines a variation of position by detecting a distance with respect to at least one part of the body of the person wearing the ambulation assistance wearable device,
wherein said at least one measuring member determines the variation of the position by acting with respect to a reference outside of the person wearing the ambulation assistance wearable device, and
wherein said at least one measuring member is secured to said at least one support in a substantially outer side position or a substantially inner side position with respect to a plane of sagittal symmetry of the person or substantially at said plane of sagittal symmetry.

12. The ambulation assistance wearable device according to claim 11, wherein said at least one measuring member uses reflection phenomena to determine translation and/or rotation in space.

13. The ambulation assistance wearable device according to claim 11, wherein said at least one measuring member determines the variation of the position by acting with respect to a floor and/or with respect to at least one flat surface positioned parallel to a plane in front of the person, said at least one flat surface being at a predetermined distance with respect to said plane upon starting the ambulation.

14. The ambulation assistance wearable device according to claim 11, wherein said at least one measuring member is integrally positioned with said at least one light source and/or anchored on said at least one support.

15. An ambulation assistance wearable device, comprising:
at least one support, adapted to be removably attached to a body of a person in an attachment position;
at least one power supply, anchored to said at least one support;
at least one light source, mounted on said at least one support and electrically connected to said at least one power supply, said at least one light source being configured, in use, to emit at least one beam of visible light towards a ground, at least at one front stepping point to which the person has to move a foot, in order to move forward along an ambulation direction;
at least one sensor means configured to detect at least one control parameter identifying an ambulation condition;
at least one processing unit operatively connected to said at least one power supply, said at least one light source and said at least one sensor and configured to control an activation-deactivation of said at least one light source, as a function of said at least one control parameter, corresponding to an angle or to a displacement measurement related to an instant position of at least one part of the body wearing the ambulation assistance wearable device during ambulation;
at least one measuring member configured to measure, save, and/or transmit a linear or an angular variation of the position of at least one part of the body of the person, to which assistance to ambulation makes is provided, wherein said at least one control parameter is determined at least at one time instant and at least as a function of said at least one measuring member of the linear and/or the angular variation of the position of at least one part of the body of the person, to whom the said assistance to the ambulation is provided;

further comprising at least one additional local support system including:

at least one second power supply, at least one energy transfer unit, at least one second processing unit comprising at least one electronic processor, at least one non-volatile storing unit, at least one volatile storing unit, at least one module for receiving information coming from the ambulation assistance wearable device, said at least one module being configured to operate with electromagnetic signals propagated in different ways, even concurrently, at least one graphic processing unit with at least one display unit, at least one algorithm that processes data coming from the at least one sensor, operative steps and instructions of said at least one algorithm being encoded as part of a processing program that can be called up and executed by said at least one additional local support system, said at least one additional local support system being configured so that, following execution of the operative steps of said at least one algorithm, predictive and/or corrective actions supplementing said at least one control parameter are defined, said actions contributing to an operation of the ambulation assistance wearable device depending on a behavior of the ambulation assistance wearable device and/or of the body to which the ambulation assistance wearable device is applied.

16. The ambulation assistance wearable device according to claim 15, wherein the information detected and/or processed by a recharging station are transferred to a remote storing and processing unit, said remote storing and processing unit being accessible by external users.

17. The ambulation assistance wearable device according to claim 16, wherein the information is transferred with commercial telecommunications systems.

18. A method of assisting ambulation of a person with an ambulation assistance wearable device according to claim 1, comprising the steps of:

generating at least one electric signal of at least one waveform having known characteristics;

transducing said at least one signal into a form adapted to be transported into empty space as a waveform propagated on a transmission medium contained in said empty space;

emitting said waveform in at least one direction and towards known and predetermined directions with reference to a transverse anatomical plane passing through a region of a body where the ambulation assistance wearable device is worn;

receiving at least one reflected waveform coming from a reflection of said waveform transmitted by remote surfaces;

transducing said reflected waveform into an electric reflection signal adapted to be processed by the ambulation assistance wearable device;

processing the electric reflection signal, the step of processing comprising filtering and recognizing steps of the characteristics of said transmitted waveform, in order to determine characteristics of a path covered by said emitted waveform and said reflected waveform;

storing said characteristics of the path covered by said emitted and reflected waveforms in one or more forms and/or in one or more supports adapted to store, temporarily or permanently, descriptive parameters of said characteristics of the path;

repeating the preceding steps at one or more predefined time periods, said one or more predefined time periods being comprised between 1 millisecond and 10 seconds;

comparing said characteristics of the path covered by said emitted and reflected waveforms detected at said predefined time intervals so that to outline a distance and/or angle variations over time;

storing and/or transferring, towards the unit managing remote data, information relative to said distance and/or angle variations over time; and varying descriptive parameters of the at least one light source in order to validate or modify a pointing to the ground of said at least one light source.

19. The method according to claim 18, wherein emitting said waveform comprises emitting said waveform by two or more sources positioned adjacently to a knee and arranged within a plane substantially parallel to a transversal plane of the body of the person, to cover within said plane an angular interval in a range from 0° to 360, a corresponding arc being centered on a side to side axis of the person and oriented towards an opposite knee.

20. The method according to claim 19, wherein said sources emit said waveforms towards said remote surfaces, said remote surfaces being substantially flat and substantially parallel to a sagittal plane of the body of the person.

* * * * *